(12) United States Patent
Dubey et al.

(10) Patent No.: US 7,811,239 B2
(45) Date of Patent: Oct. 12, 2010

(54) CERVICAL DILATION MEASUREMENT APPARATUS

(75) Inventors: Dharmesh Dubey, Jacksonville, FL (US); Tim Baird, Vedra Beach, FL (US)

(73) Assignee: Intrapartum, LLC, Jacksonville, FL (US)

( * ) Notice: Subject to any disclaimer, the term of this patent is extended or adjusted under 35 U.S.C. 154(b) by 32 days.

(21) Appl. No.: 11/401,749

(22) Filed: Apr. 11, 2006

(65) Prior Publication Data

US 2007/0255185 A1 Nov. 1, 2007

Related U.S. Application Data

(63) Continuation-in-part of application No. 11/321,061, filed on Dec. 29, 2005.

(51) Int. Cl.
*A61B 5/103* (2006.01)
*A61B 5/117* (2006.01)

(52) U.S. Cl. .................. 600/591; 600/488; 600/587; 73/866.5

(58) Field of Classification Search .......... 600/591, 600/488, 587; 73/866.5; 345/158
See application file for complete search history.

(56) References Cited

U.S. PATENT DOCUMENTS

| | | | |
|---|---|---|---|
| 2,642,672 A | 6/1953 | Lewis et al. | |
| 2,924,220 A | 2/1960 | Von Micsky | |
| 3,273,559 A | 9/1966 | Evans | |
| 3,606,879 A | 9/1971 | Estes | |
| 3,626,949 A | 12/1971 | Shute | |
| 3,643,651 A | 2/1972 | Cuadros | |
| 3,768,459 A | 10/1973 | Cannon et al. | |
| 4,141,345 A | 2/1979 | Allen et al. | |
| 4,207,902 A | 6/1980 | Krementsov | |
| 4,245,656 A | 1/1981 | Farr et al. | |
| 4,362,167 A | 12/1982 | Nicolai et al. | |
| 4,611,603 A | 9/1986 | Kelso et al. | |
| 4,682,609 A | 7/1987 | Parsons | |
| 4,719,925 A | 1/1988 | Parsons | |
| 4,805,628 A | 2/1989 | Fry et al. | |
| 4,986,980 A | 1/1991 | Jacobsen | |
| 5,012,817 A * | 5/1991 | Zeilinski et al. ............. | 600/557 |
| 5,143,505 A | 9/1992 | Burdea et al. | |
| 5,222,485 A | 6/1993 | Jerath | |

(Continued)

FOREIGN PATENT DOCUMENTS

DE 4137751 A1 5/1993

(Continued)

*Primary Examiner*—Max Hindenberg
*Assistant Examiner*—Sean P Dougherty
(74) *Attorney, Agent, or Firm*—Christopher & Weisberg, P.A.

(57) ABSTRACT

The present invention provides a medical device for measuring cervical dilation, where the medical device is positionable about a hand having first and second fingers, with each finger having a tip and a side surface. The medical device may include a housing, a first extension element movably coupled to the housing, a second extension element movably coupled to the housing, and a dilation indication mechanism to measure a distance between the first and second extension elements. The medical device may also include a first lateral pressure sensor positionable about a side surface of the first finger, a second lateral pressure sensor positionable about a side surface of the second finger, a third pressure sensor positionable about a tip of the first finger, and a fourth pressure sensor positionable about a tip of the second finger.

10 Claims, 11 Drawing Sheets

U.S. PATENT DOCUMENTS

| | | | |
|---|---|---|---|
| 5,275,169 A | 1/1994 | Afromowitz et al. | |
| 5,301,680 A | 4/1994 | Rosenberg | |
| 5,354,162 A | 10/1994 | Burdea et al. | |
| 5,373,846 A | 12/1994 | Widder | |
| 5,373,852 A | 12/1994 | Harrison et al. | |
| 5,405,356 A | 4/1995 | Hahn et al. | |
| 5,406,961 A | 4/1995 | Artal | |
| 5,438,996 A | 8/1995 | Kemper et al. | |
| 5,450,857 A | 9/1995 | Garfield et al. | |
| 5,658,295 A | 8/1997 | Krementsov | |
| 5,713,371 A | 2/1998 | Sherman et al. | |
| 5,807,281 A | 9/1998 | Welch | |
| 5,807,376 A | 9/1998 | Viola et al. | |
| 5,829,438 A | 11/1998 | Gibbs et al. | |
| 5,851,188 A | 12/1998 | Bullard et al. | |
| 5,867,831 A | 2/1999 | Husain | |
| 5,876,357 A | 3/1999 | Tomer | |
| 5,935,061 A | 8/1999 | Acker et al. | |
| 6,039,701 A | 3/2000 | Sliwa et al. | |
| 6,066,104 A * | 5/2000 | Dao et al. | 600/588 |
| 6,123,923 A | 9/2000 | Unger et al. | |
| 6,200,279 B1 | 3/2001 | Paltieli | |
| 6,231,834 B1 | 5/2001 | Unger et al. | |
| 6,261,247 B1 | 7/2001 | Ishikawa et al. | |
| 6,270,458 B1 | 8/2001 | Barnea | |
| 6,275,213 B1 * | 8/2001 | Tremblay et al. | 345/156 |
| 6,363,271 B1 | 3/2002 | Berry | |
| 6,371,051 B1 * | 4/2002 | Klein et al. | 119/200 |
| 6,383,137 B1 | 5/2002 | Berry | |
| 6,419,646 B1 | 7/2002 | Baxter-Jones | |
| 6,423,000 B1 | 7/2002 | Berry | |
| 6,423,016 B1 | 7/2002 | Hamilton et al. | |
| 6,450,977 B1 | 9/2002 | Baxter-Jones | |
| 6,524,249 B2 | 2/2003 | Moehring et al. | |
| 6,526,669 B2 | 3/2003 | Nagata | |
| 6,567,990 B1 | 5/2003 | Spitznagle | |
| 6,569,108 B2 | 5/2003 | Sarvazyan et al. | |
| 6,592,315 B2 | 7/2003 | Osborne, Jr. | |
| 6,669,653 B2 | 12/2003 | Paltieli | |
| 6,802,817 B2 | 10/2004 | Baxter-Jones et al. | |
| 6,866,643 B2 | 3/2005 | Kramer | |
| 7,042,438 B2 | 5/2006 | McRae et al. | |
| 7,150,108 B2 | 12/2006 | Babb | |
| 2001/0039388 A1 | 11/2001 | Korotko et al. | |
| 2001/0040550 A1 | 11/2001 | Vance et al. | |
| 2002/0075232 A1 * | 6/2002 | Daum et al. | 345/158 |
| 2003/0114779 A1 | 6/2003 | Paltieli | |
| 2003/0125629 A1 * | 7/2003 | Ustuner | 600/459 |
| 2003/0229267 A1 | 12/2003 | Belson et al. | |
| 2004/0068203 A1 | 4/2004 | Gellman et al. | |
| 2004/0210136 A1 | 10/2004 | Varghese et al. | |
| 2004/0225235 A1 | 11/2004 | Ben-Cnaan et al. | |
| 2004/0236193 A1 | 11/2004 | Sharf | |
| 2005/0027215 A1 | 2/2005 | Baxter-Jones et al. | |
| 2005/0038340 A1 | 2/2005 | Vaezy et al. | |
| 2005/0049509 A1 | 3/2005 | Mansour et al. | |
| 2006/0025690 A1 * | 2/2006 | Guigne et al. | 600/459 |
| 2006/0089668 A1 * | 4/2006 | Warburton | 606/203 |
| 2006/0094989 A1 * | 5/2006 | Scott et al. | 601/5 |
| 2006/0129070 A1 | 6/2006 | Pearl et al. | |

FOREIGN PATENT DOCUMENTS

| | | |
|---|---|---|
| EP | 0752 233 | 1/1997 |
| GB | 2 137 499 A | 10/1984 |
| GB | 2137499 A | 10/1984 |
| WO | 9742871 A1 | 11/1997 |
| WO | 9809565 A1 | 3/1998 |
| WO | WO 98/09565 A | 3/1998 |
| WO | 2004006767 A2 | 1/2004 |
| WO | WO 2004/006767 A | 1/2004 |
| WO | 2004062526 A2 | 7/2004 |
| WO | WO 2004/062526 A | 7/2004 |
| WO | 2005020814 A1 | 3/2005 |
| WO | WO 2005/020814 A | 3/2005 |
| WO | 2005070061 A2 | 8/2005 |
| WO | WO 2005/084745 A | 9/2005 |

* cited by examiner

CERVICAL DILATION MEASUREMENT APPARATUS

CROSS-REFERENCE TO RELATED APPLICATION

This application is a continuation-in-part of U.S. patent application Ser. No. 11/321,061, filed Dec. 29, 2005, entitled CERVIMETER, the entirety of which is incorporated herein by reference.

STATEMENT REGARDING FEDERALLY SPONSORED RESEARCH OR DEVELOPMENT n/a

FIELD OF THE INVENTION

The present invention relates to obstetric devices and more particularly, to a method and apparatus for measuring cervical dilation during pregnancy.

BACKGROUND OF THE INVENTION

During the later stages of pregnancy, the cervix typically undergoes numerous physical changes which provide increased safety and ease with which the fetus can be delivered. Particularly, the cervical canal tissue softens and increases in pliability, and subsequently, the diameter of the cervical canal begins to increase. Eventually, the dilation of the cervix is completed, allowing for the unobstructed passage of the fetus.

Cervical diameter is monitored throughout labor and is instrumental in diagnosing such conditions as dysfunctional or arrested labor, to determine whether labor augmentation or a cesarean section should be performed, as well as to establish whether or when various pharmaceutical agents should be administered. Physical examination of the cervical diameter is generally performed by inserting two fingers into the vagina and up to the cervix. Upon reaching the cervix, the fingers are spread apart to determine the approximate dilated diameter. While an obstetrician may be fairly experienced in performing a manual cervical diameter measurement, the accuracy of such a measurement can be highly subjective and can further vary depending on the particular experience, judgment, and even finger size of the attending physician. Considering the importance of the cervical dilation measurement in assessing labor progression, it is crucial to provide dilation information that is precise as well as reproducible among different healthcare providers or physicians.

Given the subjectivity and probability of inaccurate or imprecise dilation measurements, it would be desirable to provide for the precise and accurate attainment of cervical dilation measurements on a repeat basis during the course of labor.

SUMMARY OF THE INVENTION

The present invention advantageously provides a method and system for the accurate and precise measuring of cervical dilation during labor. The medical device may include an elongate body defining a proximal end and a distal end, with the elongate body further including an inflation lumen. An expandable element may be coupled to the elongate body in fluid communication with the inflation lumen, and an array of movable elements may be circumferentially disposed about the elongate body, with the array of movable elements being movably coupled to the elongate body by a plurality of wires. The medical device may also include a measurement mechanism able to determine a radial spacing of the array of movable elements, where the measurement mechanism can include a tension ring coupled to the plurality of wires. In addition, a dilation indicator can be provided in communication with the measurement mechanism, while at least one pressure sensor may be coupled to at least one of the array of movable elements. Moreover, a distal pressure sensor can be coupled to the distal end of the elongate body, with the medical device also providing a control element in communication with the at least one pressure sensor and the distal pressure sensor. The medical device can also include an inflation source in fluid communication with the expandable element, as well as an exhaust valve in fluid communication with the expandable element. Furthermore, the medical device may include a camera as well as a lighting element coupled to the distal end of the elongate body, thereby providing visual feedback to aid in the positioning of the device.

In an alternative embodiment, the present invention also provides a cervical dilation sensor to aid in the manual, two-finger approach commonly employed. The cervical dilation sensor may include a first rod, a second rod, and a sensor housing. The first and second rods may be rotatably and pivotably coupled to the sensor housing, as to freely move about the housing in at least two planes of motion. The sensor housing may include one or more sensors coupled to the first and second rods as to measure the relative movement of the two rods, while the cervical dilation sensor may also include a control monitor in communication with the one or more sensors in the sensor housing for displaying and monitoring information provided by the sensors.

Further, the cervical dilation sensor may be coupled to the hand of a physician along with additional sensors located at the fingertips of the hand to provide feedback when in contact with the head of the baby, as well as laterally mounted sensors positioned on the sides of the fingers to provide monitoring and feedback of the pressure applied on the cervical OS when the fingers are expanded. Such combination of sensors allow for precise and accurate measurements of the cervical dilation, as well as providing feedback on the fetal descent through the various stages of labor.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
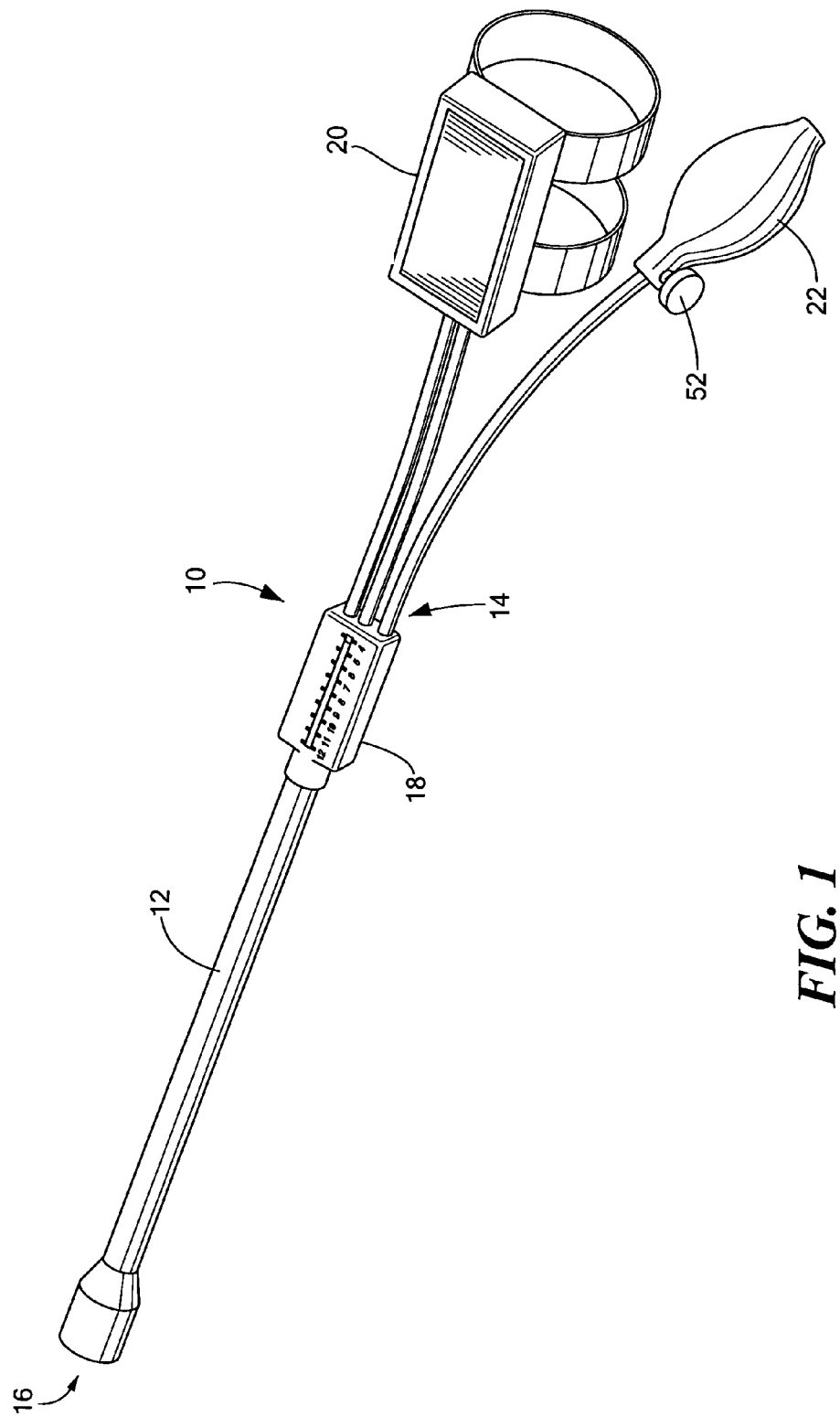
FIG. 1 is an illustration of an embodiment of a medical device in accordance with the present invention.

As shown in FIG. 1, the present invention provides a medical device 10 for measuring cervical dilation. The medical device 10 includes an elongate body 12 defining a proximal end 14 and a distal end 16. The medical device 10 may further include a dilation indicator 18 coupled to the proximal end 14 of the elongate body 12 that is capable of providing a visual indicator of the dilation measurement made by the medical device 10, as well as a control element 20 and an inflation source 22, which will be discussed in more detail below.

Figure 2:
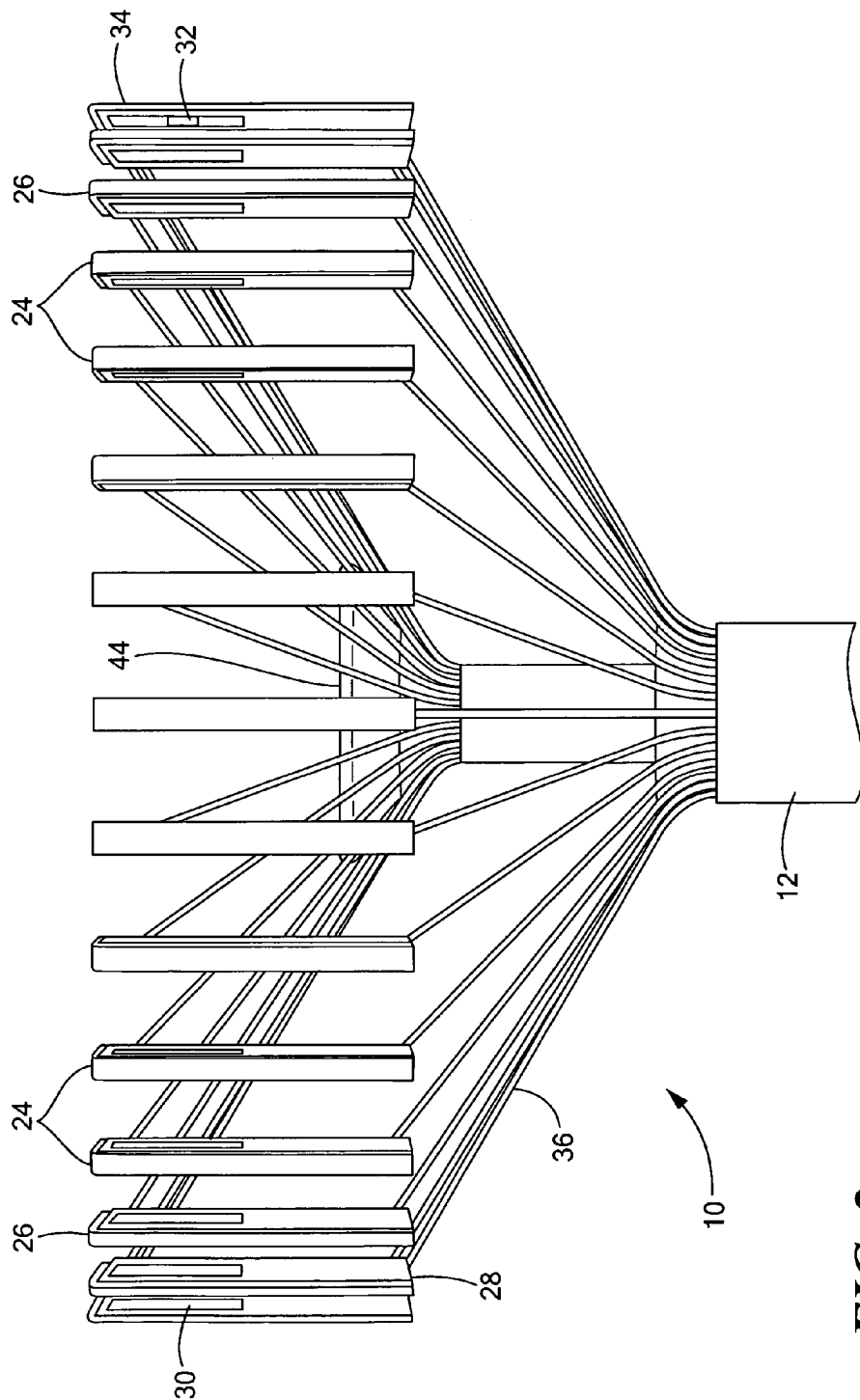
FIG. 2 is a side view of a distal end of the medical device of FIG. 1.

Now referring to FIG. 2, the medical device 10 may further include an array of movable elements 24 disposed circumferentially about an axis of the elongate body 12, where the array of movable elements 24 is located in proximity to the distal end 16 of the elongate body 12. The array of movable elements 24 are movable in a radial direction as to expand and contact with the tissue of the cervix when positioned for measurement of cervical dilation. Moreover, the array of movable elements 24 may be retracted upon completion of the desired measurement to ease the withdrawal of the medical device 10 from the patient. Each movable element may define an upper portion 26 and a lower portion 28. In addition, each movable element may define a channel 30 such that one or more pressure sensors 32 may be mounted or otherwise positionable within the channel 30 of the movable element. Moreover, an outer cushion 34 may be coupled to an outer surface of each movable element, where the outer cushion 34 may be constructed from a gel-like material or other suitable padding. The array of movable elements 24 may further be movably coupled to the elongate body 12 of the medical device 10 by a plurality of wires 36 coupled to the upper and lower portion 28 of the movable elements 24, where the plurality of wires 36 further extend through a length of the elongate body 12.

Figure 3:
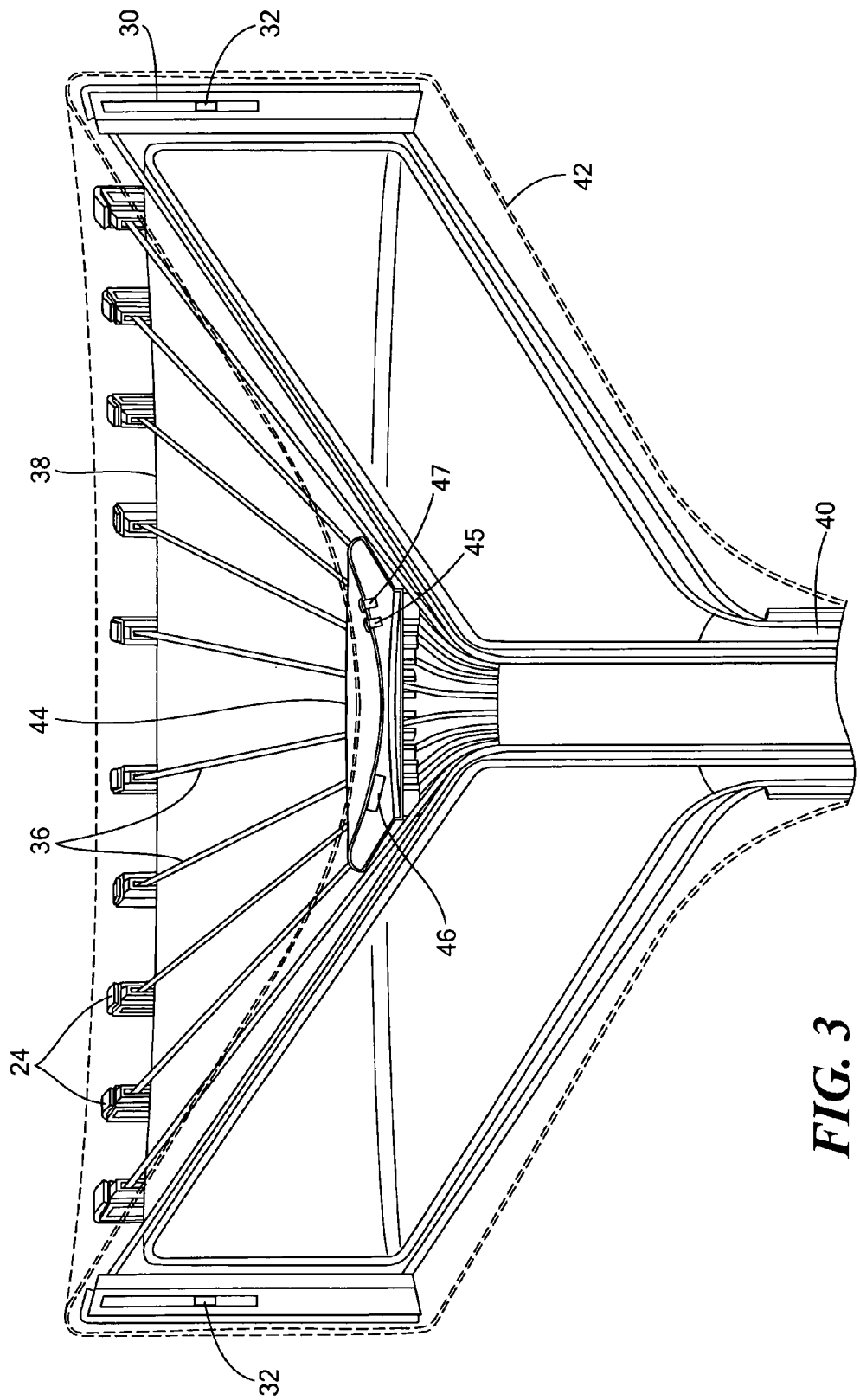
FIG. 3 is a cross-sectional view of a distal end of the medical device of FIG. 1.

While the array of movable elements 24 may be extended and retracted by manipulating the plurality of wires 36, an actuating mechanism may be provided to facilitate movement of the array of movable elements 24 from a retracted position to an extended position, and vice versa. The actuating mechanism may include a spring mechanism, a telescoping element, or, alternatively, the medical device 10 may include an expandable element 38, such as a balloon. Now referring to FIG. 3, the medical device 10 of the present invention may further include the expandable element 38 coupled to or otherwise disposed on the elongate body 12 at or near the distal end 16 of the elongate body 12. The expandable element 38 may be configured in a myriad of shapes, including a toroidal configuration in which the expandable element 38 defines a ring-like, "O" shape. Moreover, an inflation lumen 40 can be included in fluid communication with the expandable element 38, where the inflation lumen 40 is disposed within and traverses a substantial length of the elongate body 12.

The medical device 10 of the present invention may include additional features providing safety, ease of use, and the like. For example, the medical device 10 may include a protective sheath 42 encasing at least a portion of the distal end 16 of the elongate body 12. The sheath 42 may include one or more layers of various materials to provide a water-tight seal around the medical device, as well as adding to patient comfort by having additional padding and/or a lubricious coating to ease positioning of the device. Furthermore, a distal pad 44 may be coupled to the elongate body 12 at or near the distal end 16, where the distal pad 44 may be contoured or shaped to conform to the curvature of the head of a baby. In addition, a distal pressure sensor 46 may be coupled to the distal pad 44 to aid in monitoring the positioning of the medical device 10 and for determining contact with the baby. The distal pad 44 and distal pressure sensor 46 may provide feedback to a physician and aid in the axial positioning of the medical device 10 upon insertion into a patient. Furthermore, a camera 45 and a lighting element 47 may also be coupled to the distal portion of the medical device. The camera 45 may be a miniaturized instrument or pin-hole camera as commonly employed in endoscopic surgical procedures, while the lighting element 47 may include a diode, fiber optic, or other illumination mechanism as is known in the art. The camera 45 and lighting element 47 may provide visual feedback to a physician to further aid in maneuvering and positioning the medical device when in use.

Figure 4:
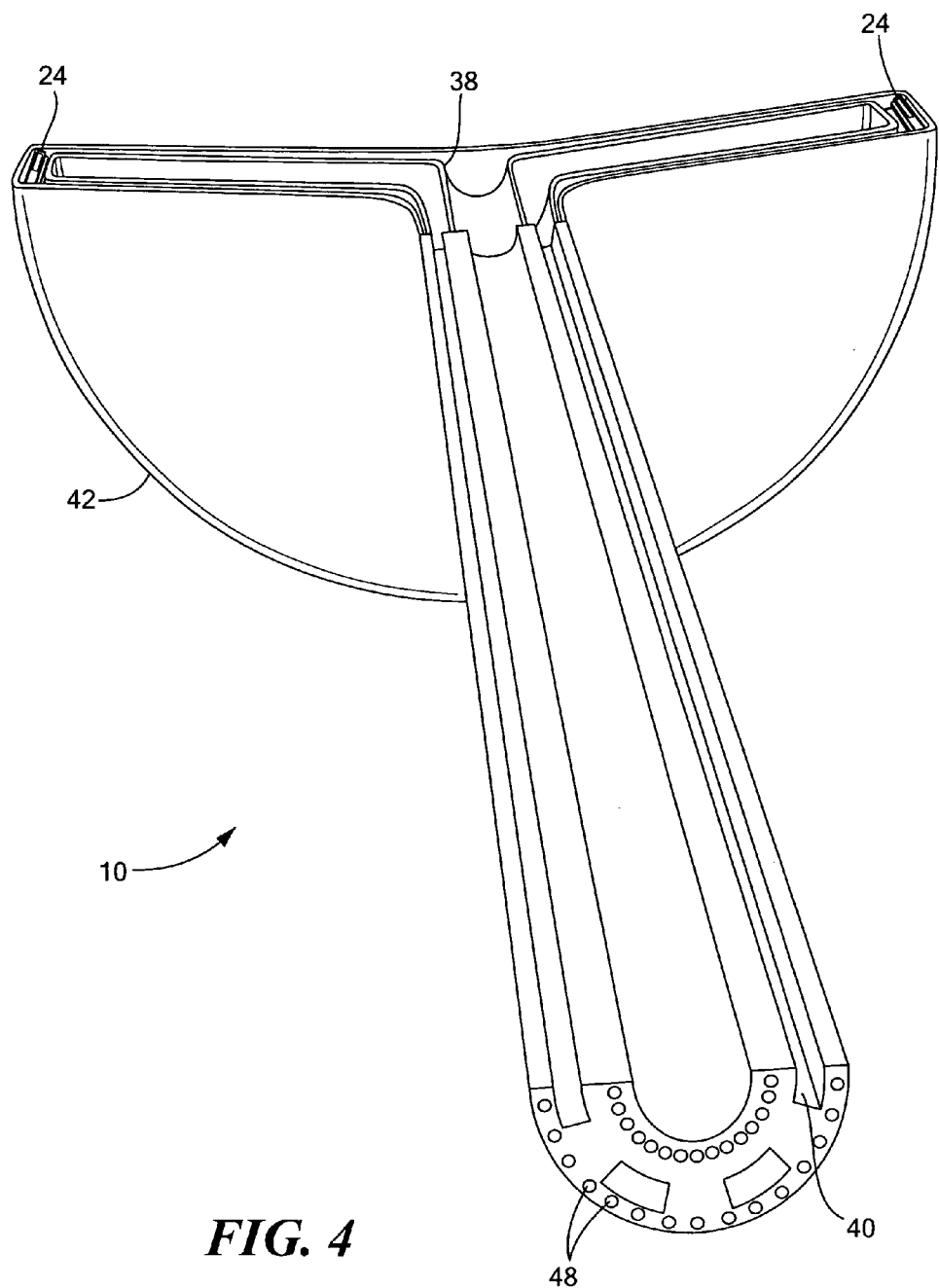
FIG. 4 is an additional cross-sectional view of the medical device of FIG. 1.

As shown in FIG. 4, the elongate body 12 may define a plurality of wire lumens 48 for slideably receiving a portion of each of the plurality of wires 36 coupled to the array of movable elements 24. Each wire of the plurality of wires 36 may be slideably positioned within each of the plurality of wire lumens 48 as to slide freely with little friction, thereby facilitating the movement of the array of movable elements 24 when the medical device 10 is in use. The wires 36 may have sufficient length as to extend through the entire length of the respective wire lumens 48, and may further extend out of the proximal end 14 of the elongate body 12.

Figure 5:
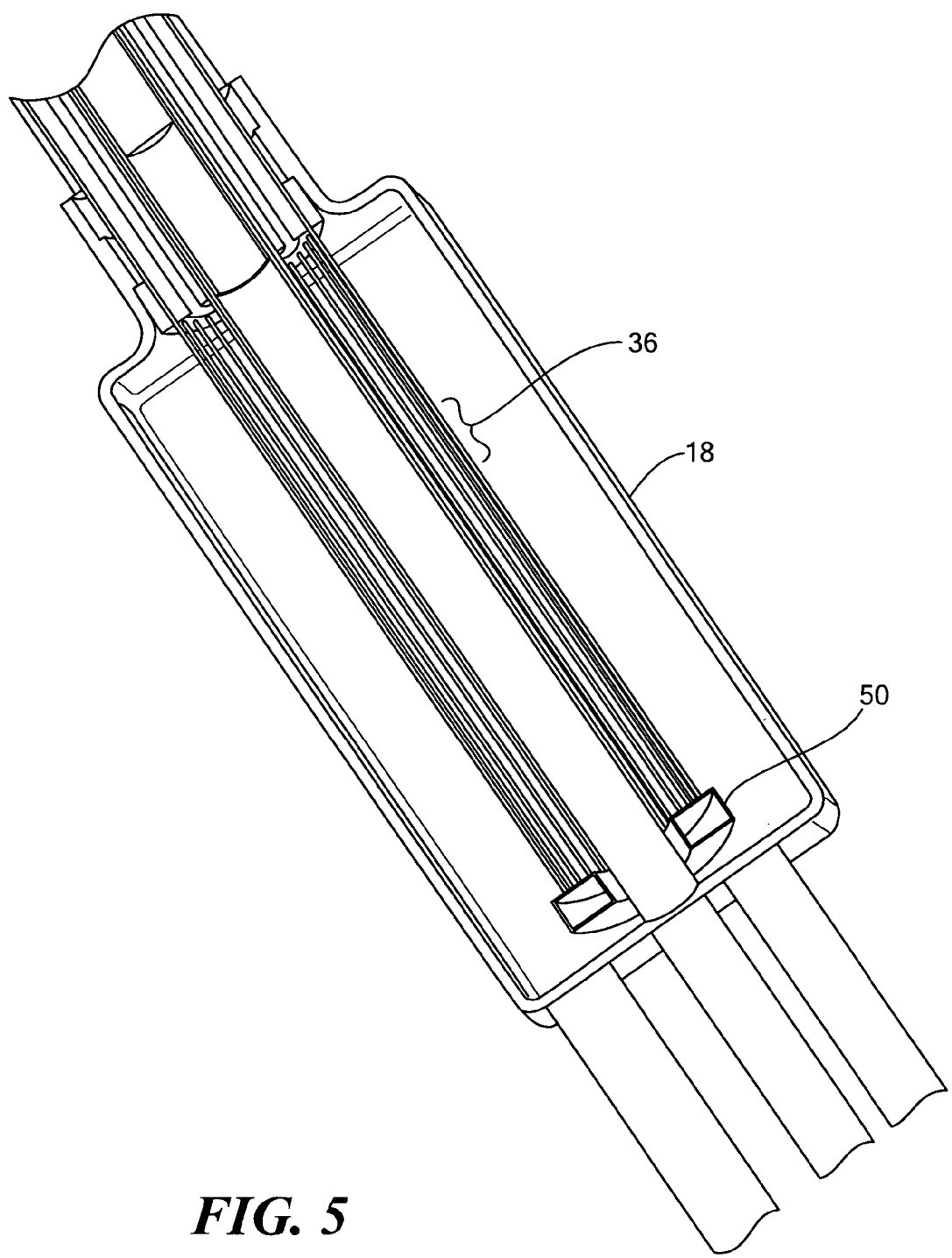
FIG. 5 is a cross-sectional view of an embodiment of a dilation indicator in accordance with the present invention.

The medical device 10 of the present invention may further include a measurement mechanism for monitoring and/or quantifying the movement of the array of movable elements 24 when the medical device 10 is in use. For example, as shown in the FIG. 5 illustration of a cross-section of the dilation indicator 18, the medical device 10 may include a tension ring 50 coupled to the plurality of wires 36 such that the tension ring 50 moves as the wires 36 extend and retract in response to the movement of the array of movable elements 24. The tension ring 50 may further be slideably coupled to the dilation indicator 18, where the dilation indicator 18 conveys a dilation measurement in response to the relative motion of the tension ring 50, the plurality of wires 36, and thus, the array of movable elements 24. The dilation indicator 18 may include predetermined values calculated from the movement of the tension ring 50 as to eliminate the need for a physician to do any calculating to determine the dilation measurement.

Again referring to FIG. 1, in an exemplary system, the proximal end 14 of the medical device 10 of the present invention is coupled to the control element 20 which may be in communication with the numerous sensors provided on the medical device 10, and may also include a visual display to indicate the various operating characteristics and feedback from the device and the included sensors. The control element 20 may include an external console or may further include a wrist-mounted device to ease the overall use of the medical device 10, and may also be in communication with the camera 45 and lighting element 47 coupled to the distal end of the medical device 10. In addition, the inflation source 22 can be provided which may be coupled to the inflation lumen 40 at the proximal end 14 of the elongate body 12, where the inflation source 22 is able to provide a fluid or gas into the inflation lumen 40 for subsequent delivery to the expandable element 38. Examples of suitable inflation source 22s include manual pumps, powered pumps, or the like. Moreover, an exhaust valve 52 may be in fluid communication with both the inflation source 22 as well as the inflation lumen 40 for subsequent control of the release of fluid from the medical device 10.

Figure 6:
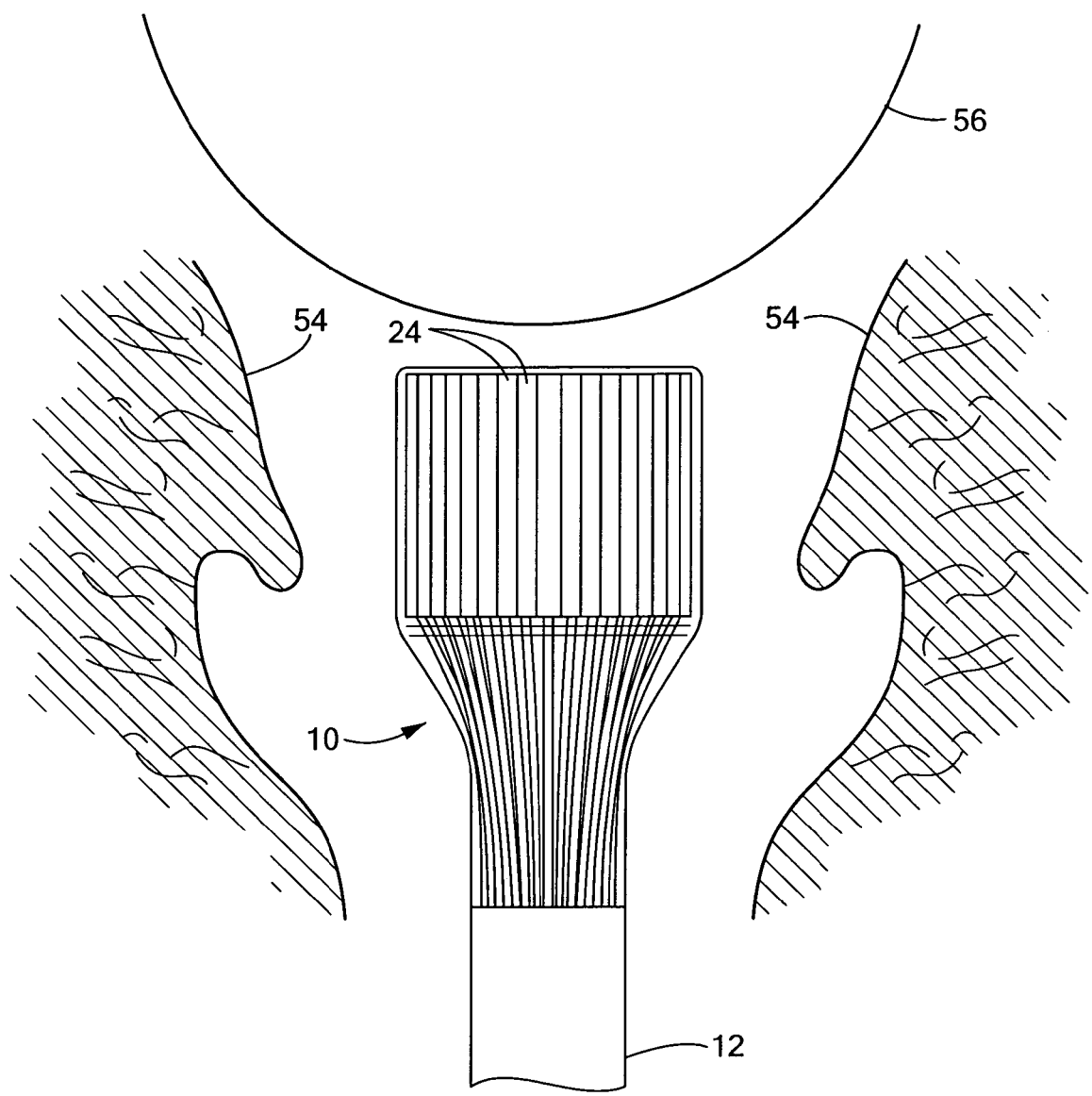
FIG. 6 is an illustration of a distal end of a medical device in a deflated state in accordance with the present invention.
Figure 7:
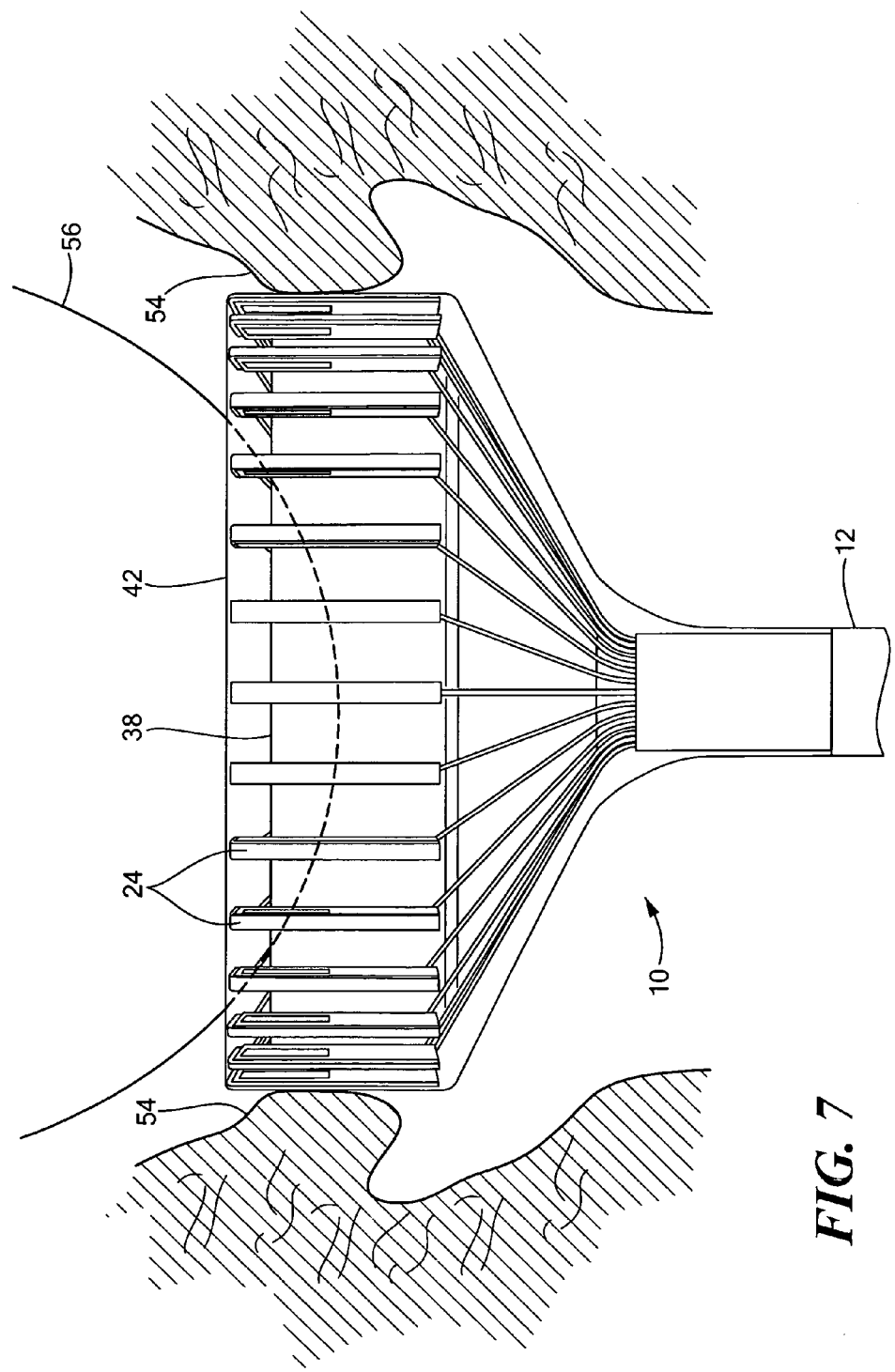
FIG. 7 is an illustration of a distal end of a medical device in an inflated state in accordance with the present invention.
Figure 8:
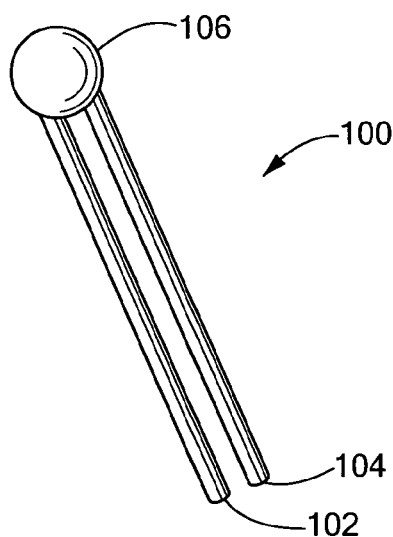
FIG. 8 is a perspective illustration of an embodiment of a cervical dilation sensor in accordance with the present invention.
Figure 9:
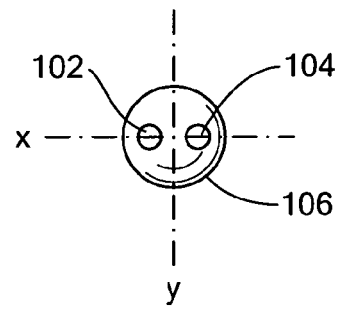
FIG. 9 is a side view of the cervical dilation sensor of FIG. 8.
Figure 10:
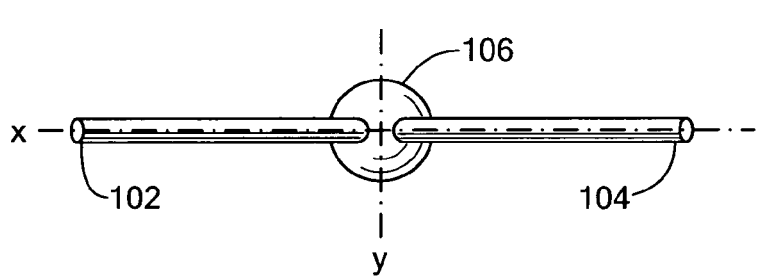
FIG. 10 is an additional illustration of the cervical dilation sensor of FIG. 8.
Figure 11:
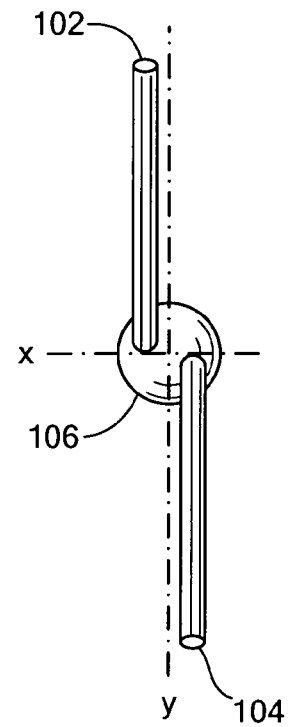
FIG. 11 is yet another depiction of the cervical dilation sensor of FIG. 8.

Referring now to FIGS. 6 and 7, in an exemplary use of the medical device 10 of the present invention, a precise dilation measurement may be performed during the various stages of labor. The medical device 10, in a deflated state, may be positioned such that the distal end 16 of the elongate body 12 is in proximity to the dilated region of the cervix 54. Proper positioning can be aided by feedback provided by the distal pressure sensor 46 when contacting the head 56 of the baby, as well as monitoring the visual feedback from the camera 45. Upon proper positioning, the array of movable elements 24 may be extended to contact the tissue of the cervix 54, for example, by actuating the inflation source 22 to inflate the expandable element 38. As the expandable element 38 is inflated and subsequently expands, the array of movable elements 24 located around the periphery of the expandable element 38 will move outward in a radial direction, while lengths of the plurality of wires 36 will be drawn further into the respective plurality of wire lumens 48. As the array of movable elements 24 is coupled to the plurality of wires 36, which are further coupled to the tension ring 50, the expandable element 38 will expand outward uniformly from the elongate body 12.

The inflation source 22 may continue to inflate the expandable element 38 until the movable elements 24 of the medical device 10 come into contact with the dilated cervix 54. Such contact can be indicated and monitored through information provided by the pressure sensors 32 coupled to the movable elements 24. Furthermore, the control element 20, which is in communication with the sensors, may include an algorithm or computational ability to determine if the pressure sensor feedback indicates a substantially uniform circular state. That is to say, that the pressure measurements from each of the pressure sensors 32 disposed about the movable elements 24 are approximately the same. When the desired inflation level has been attained as indicated by pressure sensor measurements, the inflation source 22 may be deactivated, or, alternatively, the exhaust valve 52 may be triggered to prevent additional fluid from entering the expandable element 38. Once appropriately inflated, the measuring mechanism and the dilation indicator 18 can provide the dilation measurement as indicated by the distance the plurality of wires 36, and thus the tension ring 50, traveled in reaching the expanded state. As previously stated, the dilation indicator 18 can directly correlate the distance traveled by the wires 36, and thus, the measured expansion of the movable elements 24, to an accurate and precise dilation measurement.

Upon completion of the desired measurement, the movable elements 24 are retracted towards the elongate body 12, i.e., by deflating the expandable element 38 by opening the exhaust valve 52, upon which the movable elements 24 will retract to a closed position for the removal of the medical device 10 from the patient. Both the tension ring 50 and the plurality of wires 36 may be biased towards a closed, retracted position, such that when the expandable element 38 is not under positive inflation pressure, the medical device 10 retains a closed, retracted state. Furthermore, as described above, the medical device 10 may include an outer sheath 42 which, if used, may be removed and replaced for subsequent uses of the medical device 10, thereby providing a re-usable device while maintaining the sterility of the medical environment.

In an alternative use of the medical device 10 of the present invention, the distal portion of the medical device 10 may be positioned within the cervical region of a patient and be employed to force a safe and uniform dilation where such dilation has not occurred. The medical device 10 could be positioned in the undilated cervix and provide a controllable expansion with a relatively constant pressure provided by the expansion of the expandable element 38. Subsequently, through the monitoring of sensor feedback, the inflation pressure could be appropriately adjusted in order to achieve the desired dilation of the cervical tissue.

Now referring to FIGS. 8-11, in an alternative embodiment of the present invention, a cervical dilation measurement device 100 is provided to aid in the manual, two-finger approach of measuring cervical dilation. The measurement device 100 may include a first extension element 102, a second extension element 104, and a base or connecting element 106. The first and second extension elements 102,104 may be rotatably and pivotably coupled to the base element 106, as to freely move about the housing in at least two planes of motion. The base element 106 may include a dilation indication mechanism to measure the distance between and/or the relative movement of the two extension elements. The dilation indication mechanism may include one or more sensors coupled to or otherwise in communication with the first and second extension elements 102,104. Sensors suitable for monitoring the movement of the first and second extension elements 102,104 may include sensors mechanically coupled to the extension elements capable of measuring their displacement or movement directly, including but not limited to torque or strain gauges, or may alternatively include sensors positioned in the tips of the first and second extension elements that can monitor distance between the two tips via radiofrequency, optical energy, or the like. A third sensor may be incorporated, in the base element 106 for example, to provide increased accuracy and precision through triangulation methods. The measurement device 100 may also include the control element 20, as previously described and illustrated in FIG. 1, in communication with the base element 106 and one or more sensors for displaying and monitoring information provided by the sensors.

Figure 13:
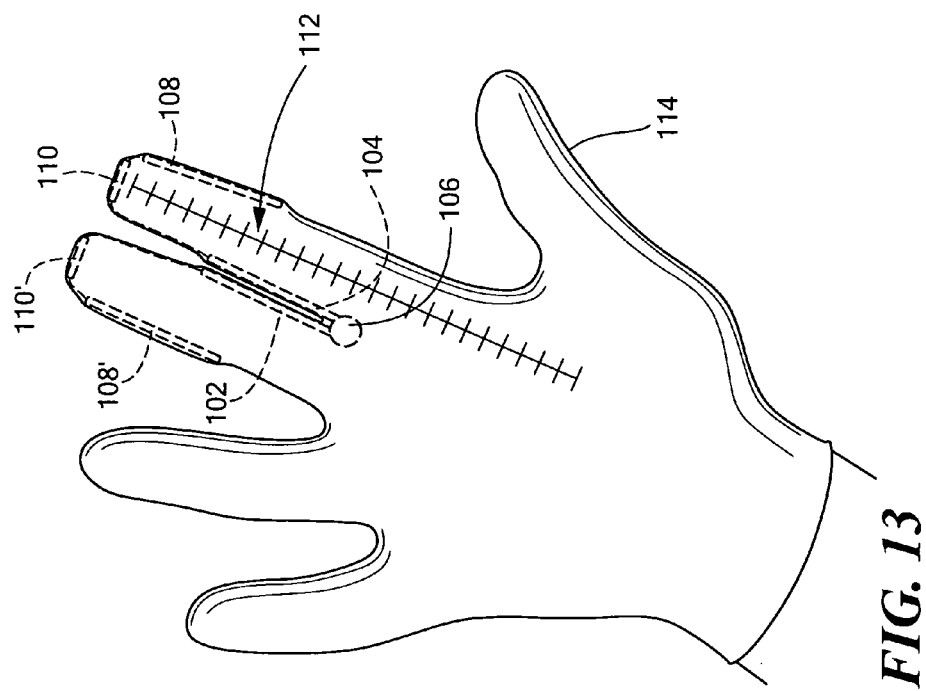
FIG. 13 depicts an embodiment of a cervical dilation sensor within a glove.
Figure 12:
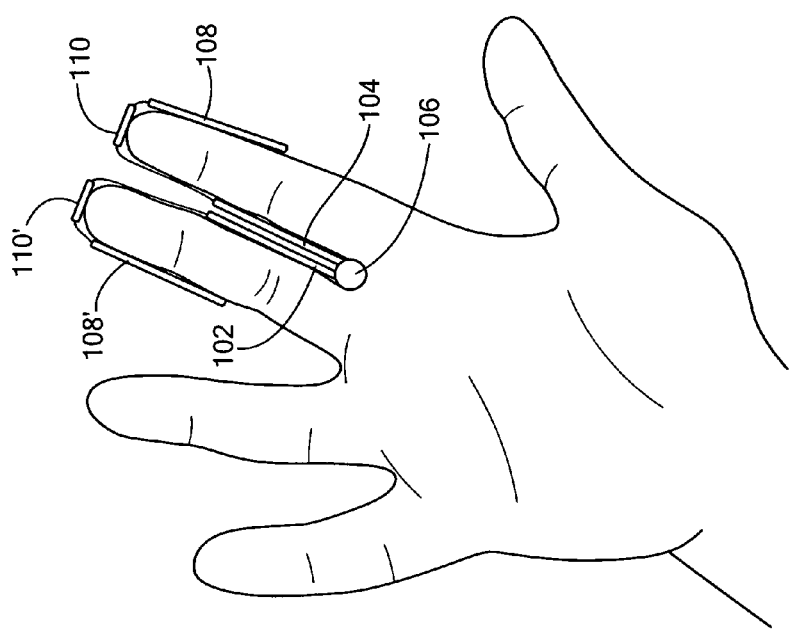
FIG. 12 shows an embodiment of a cervical dilation sensor coupled to a hand.
Figure 14:
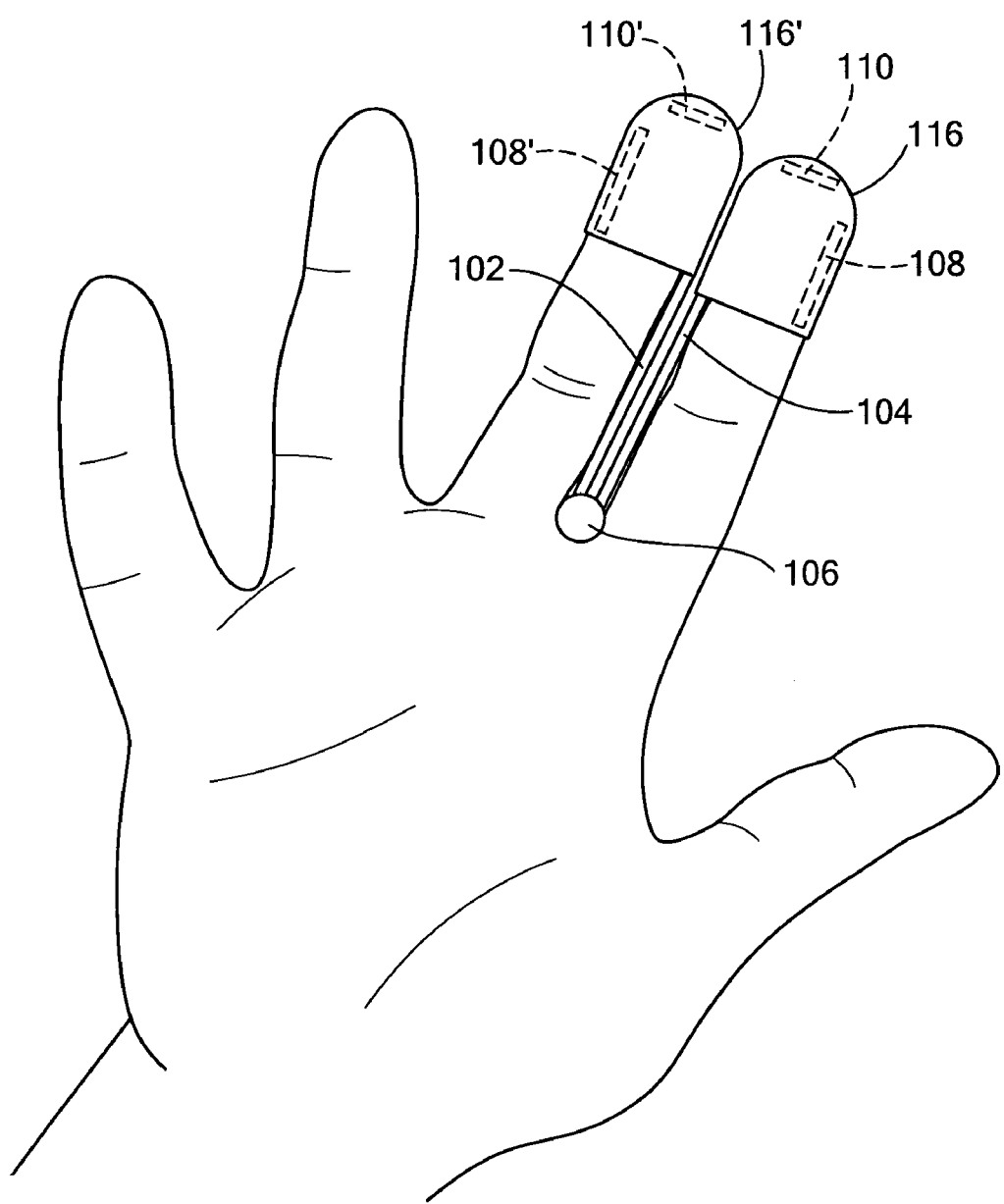
FIG. 14 illustrates an additional embodiment of a cervical dilation sensor coupled to a hand.

Now referring to FIGS. 12-14, the measurement device 100 of the present invention may also include one or more lateral sensors 108,108' positionable about the sides of the first and second fingers of a hand used in the manual cervical dilation measurement technique. For example, as shown in FIG. 12, the first finger is the index finger and the second finger is the middle finger. As used herein, the hand includes fingers, a palm portion at the proximal end of the fingers, a pad portion at the distal end of the fingers on the same face of the hand as the palm portion, an upper portion of the fingers, the upper portion being on the opposite side of the pad portion, a tip portion of the fingers, and side or lateral portions of the fingers. For example, the index finger has a side portion facing the middle finger and a side portion facing away from the middle finger, and the middle finger has a side portion facing the index finger and a side portion facing away from the index finger. The lateral sensors 108,108' may provide pressure feedback information when in contact with the cervix that may assist a physician in making a measurement while avoiding or minimizing cervical distension. As such, the reduced likelihood of cervical distension increases the ability to provide an accurate and precise dilation measurement. The lateral sensors 108,108' may include one or more thin film pressure sensors, as known in the art, to minimize the increase in width or thickness of the device, thereby providing ease of use and reducing discomfort of the patient, and may further be placed in communication with the control element 20.

The measurement device 100 of the present invention may also include one or more finger-tip pressure sensors 110,110' positionable about the tips of the first and second fingers used in the manual cervical dilation measurement technique. The finger-tip pressure sensors 110,110' may indicate pressure feedback information via the control element 20 upon contact with the head of the baby. In addition to providing feedback information to prevent excess pressure on the head of the baby, upon recognition that the finger tips are indeed contacting the head of the baby, a marker or other measurement indicator may be used to gauge the position and descent of the baby, as described below.

Historically, practitioners have used the ischial spine as the index point (0 station) for a determination of fetal descent, and assigned an arbitrary number in centimeters above and below the ischial spine. More specifically, "station" refers to the level of the presenting fetal part in the birth canal as described in relationship to the ischial spines, which are halfway between the pelvic inlet and the pelvic outlet. When the lowermost portion of the fetal presenting part is at the level of the ischial spine, it is designated as being at zero (0) station. In the past, the long axis of the birth canal has been arbitrarily divided into segments for a determination of the position of the baby. Thus, as the presenting fetal part descends from the inlet toward the pelvic outlet, the typical designation is −5, −4, −3, −2, −1, 0 station, +1, +2, +3, +4, +5. Using this method, the degree of accuracy (in centimeters) is difficult to achieve clinically. In practice, physicians may generally make an educated guess about the station of the presenting part of the baby, since after the "0" point (0 station), the baby's head covers the ischial spine point and eliminates the ability to measure and reproduce distance caudal to this point. Contrary to the typical method employed, where accuracy and precision may be difficult to maintain, the feedback from the finger-tip sensors may provide an indication of contact with the head of the baby. Upon such indication, a marking or other descent indicator 112 on the portion of the hand of the physician external to the genitalia may be used to provide an accurate and precise measurement of the location and descent of the baby. Measurements over the course of labor indicate rates of progression which are practical, relatively easier to standardize and explainable to the patient or other practitioners. This approach of measurement is termed "Advancement".

In an exemplary use, the measurement device 100 is coupled to the hand of a physician, with the first extension element 102 being paired to a first finger, the second extension element 104 being paired to a second finger, and the base element 106 being positioned in between the first and second fingers. Moreover, where the lateral sensors 108,108' or finger-tip sensors 110,110' are included, the sensors will be positioned about the sides and tips of the fingers, respectively, as described above. The coupling may be achieved through the integration of the measurement device 100 with a glove 114, or through direct adhesion of the various components to the fingers themselves. Additionally, the cervical dilation measurement device 100 may include two cap elements 116, 116' positionable about the finger tips, with the first and second extension elements 102,104 extending from the cap elements 116,116' and towards the base element 106, and with the lateral and finger-tip sensors coupled to the cap elements in the appropriate positions. Any wires or other communicative elements connecting the sensors to the control element 20 may be routed through the glove or positioned down the back of the hand as needed to provide connectivity while preventing interference with the use of the device. Alternatively, the various sensors may communicate with the control element 20 wirelessly as known in the art.

Subsequently, the physician may position the first and second fingers and the cervical dilation measurement device 100 in proximity to the cervix. Upon reaching the desired location, the two fingers can be spread either into a "V" shape or an "L" shape, and the relative movement of the first and second extension elements 102,104 may be measured by the one or more sensors in the base element 106, with the lateral sensors 108,108' preventing cervical distension as previously described. As a result, the physician will not be required to make a subjective observation as to the actual cervical dilation, as the actual width between the spread fingers can be accurately assessed by the cervical dilation measurement device 100 and provided to the physician through the control element 20. In addition, upon contacting the head of the baby with the finger-tip sensors, the descent indicator 112 may be referenced to determine the location of the baby.

Figure 15:
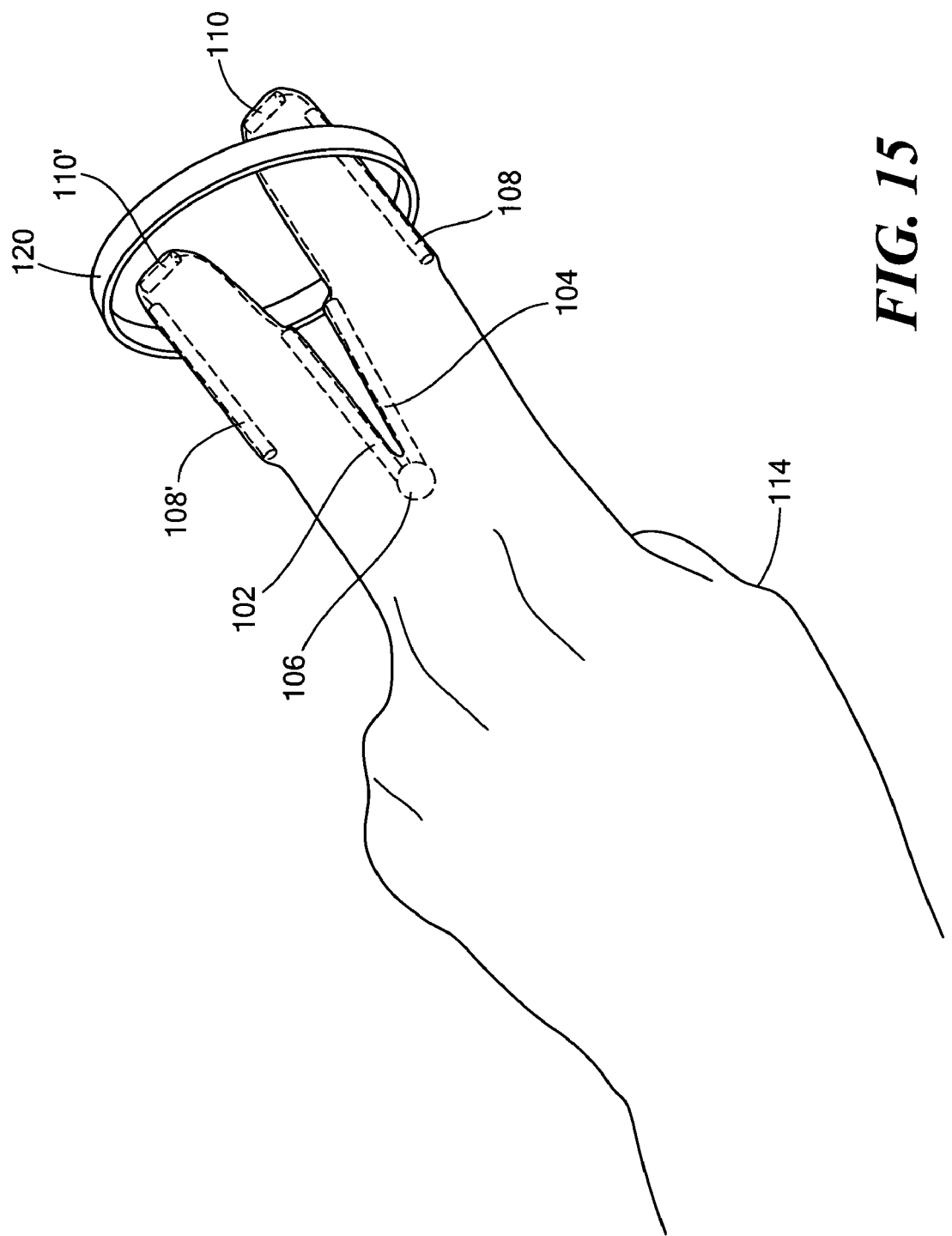
FIG. 15 shows an embodiment of a calibration element for use with a cervical dilation sensor in accordance with the present invention.

While the method of measurement as described above may provide an accurate and precise measurement of cervical dilation, it is realized that different physicians may have variations in both finger length and thickness which may affect the accuracy of the measured dilation. Now referring to FIG. 15, the present invention may include a calibration element 120 for use with the measurement device 100 to compensate for the variations in the finger dimensions of a physician. The calibration element 120 may include an object of known dimensions, thereby providing a reference value from which the measurement device 100 may be calibrated. For example, the measurement device 100 may be coupled or otherwise positioned about the hand of a physician or operator, with the first extension element 102 being paired to a first finger, the second extension element 104 being paired to a second finger, and the base element 106 being positioned in between the two fingers. Subsequently, the first and second fingers may be extended such that an outer portion of the first and second fingers contact a portion of the calibration element 120, providing a "simulated" distance measurement. Upon contacting the calibration element 120, the first and second fingers will be separated by a known distance, and the relative movement of the first and second extension elements 102,104 about the base element 106 can be appropriately modified to reflect an accurate and precise measurement. Such modification may include, for example, an algorithm or other computational calculation taking into account the known, fixed dimensions of the calibration element 120, the known length of the first and second extension elements 102, 104, as well as the angle formed between them at the intersection with the base element 106. The suggested calibration procedure may be performed a single time for each operator who may thereafter use the measurement device 100, and such values and calibration modifications may be stored in the control element 20 for ease of subsequent use without the need to re-calibrate the device. Alternatively, the suggested calibration procedure may be performed prior to each dilation measurement to ensure accuracy and precision.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device for measuring cervical dilation during delivery of a baby, the medical device being disposable within a glove and positionable about the fingers of a human hand, wherein the fingers of a human hand have an upper portion at a distal end the fingers, a palm portion at a proximal end of the fingers, a pad portion on the same face of the hand as the palm portion, a tip portion, and side portions, the medical device comprising:
   a connecting element positionable between an index finger and a middle finger at the proximal end of the fingers;
   a first extension element movably coupled to the connecting element and positionable on a side portion of the index finger that faces the middle finger, wherein the first extension element is movable about the connecting element in at least two planes of motion;
   a second extension element movably coupled to the connecting element and positionable on a side portion of the middle finger that faces the index finger, wherein the second extension element is movable about the connecting element in at least two planes of motion;
   a first pressure measurement sensor positionable on a side portion of the index finger that faces away from the middle finger;
   a second pressure measurement sensor positionable on a side portion of the middle finger that faces away from the index finger; and
   a control element in communication with one of the connecting element, first extension element, and second extension element to provide a measurement of a distance between the first and second extension elements, the control element also in communication with the first and second pressure measurement sensors.

2. The medical device according to claim 1, further comprising a first finger-tip pressure sensor in communication with the control element.

3. The medical device according to claim 2, further comprising a second finger-tip pressure sensor in communication with the control element.

4. The medical device according to claim 1, wherein the first and second extension elements are coupled to an interior of the glove.

5. The medical device according to claim 4, wherein the glove includes an indicator of a relative position of the baby to the cervix.

6. The medical device according to claim 4, wherein the first and second pressure measurement sensors are coupled to the interior of the glove.

7. The medical device according to claim 4, further comprising first and second finger-tip pressure sensors coupled to the interior of the glove and in electrical communication with the control element.

8. The medical device according to claim 1, further comprising a first cap element coupled to the first extension element, and a second cap element coupled to the second extension element.

9. The medical device according to claim 8, wherein the first pressure measurement sensor is coupled to the first cap element, and the second pressure measurement sensor is coupled to the second cap element.

10. The medical device according to claim 8, further comprising a first finger-tip pressure sensor coupled to the first cap element, and a second finger-tip pressure sensor coupled to the second cap element.

* * * * *